(12) United States Patent
Suita et al.

(10) Patent No.: US 8,230,741 B2
(45) Date of Patent: Jul. 31, 2012

(54) TEST METHOD OF OPERATIONS OF ULTRASONOGRAPH AND ULTRASOUND PROBE

(75) Inventors: Takahiro Suita, Tokyo (JP); Keisuke Kawahara, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 580 days.

(21) Appl. No.: 12/422,511

(22) Filed: Apr. 13, 2009

(65) Prior Publication Data

US 2009/0260443 A1    Oct. 22, 2009

(30) Foreign Application Priority Data

Apr. 17, 2008 (JP) ................................. 2008-107866
Apr. 9, 2009 (JP) ................................. 2009-094997

(51) Int. Cl.
*G01N 29/00* (2006.01)
*A61B 8/00* (2006.01)
(52) U.S. Cl. ............................. 73/628; 73/632; 600/437
(58) Field of Classification Search ............ 73/631–638, 73/627–629, 865.9; 600/437, 438
See application file for complete search history.

(56) References Cited

U.S. PATENT DOCUMENTS

| | | | | |
|---|---|---|---|---|
| 3,885,419 A | * | 5/1975 | Witte et al. ...................... | 73/600 |
| 4,065,960 A | * | 1/1978 | Grabendorfer et al. ......... | 73/609 |
| 5,517,994 A | * | 5/1996 | Burke et al. .................... | 600/437 |
| 5,748,496 A | * | 5/1998 | Takahashi et al. ............. | 702/183 |
| 7,028,529 B2 | * | 4/2006 | Gessert et al. .................. | 73/1.82 |
| 7,496,456 B2 | * | 2/2009 | Hiyama et al. .................. | 702/39 |
| 7,546,781 B2 | * | 6/2009 | Takahashi ..................... | 73/866.5 |
| 7,690,261 B2 | * | 4/2010 | Tanaka ............................ | 73/649 |
| 2009/0149750 A1 | * | 6/2009 | Matsumura .................... | 600/438 |

FOREIGN PATENT DOCUMENTS

| | | | |
|---|---|---|---|
| GB | 2047895 | * | 12/1980 |
| JP | S61-9584 | | 3/1986 |
| JP | 2002-159492 | | 6/2002 |

* cited by examiner

*Primary Examiner* — Helen C. Kwok
(74) *Attorney, Agent, or Firm* — Fitzpatrick, Cella, Harper & Scinto

(57) ABSTRACT

Provided is an ultrasonograph and the like capable of easily specifying defective parts of an ultrasound probe and appropriately treating the defective parts. A test method of an operation of an ultrasound probe that transmits and receives a signal of ultrasound for creating a diagnostic image in an ultrasonograph includes: bringing a test material into contact with the ultrasound probe and transmitting a first ultrasound from the ultrasound probe to the test material by a first transmitting circuit connected to the ultrasound probe; receiving, by a first receiving circuit connected to the ultrasound probe, a received signal of a reflected wave of the first ultrasound received by the test material and receiving, by a second receiving circuit connected to the test material, a received signal of the first ultrasound received by the test material; and comparing the received signals with each normal received signal stored in a memory and determining whether the operation of the ultrasound probe is normal or defective based on the comparison result.

11 Claims, 3 Drawing Sheets

FIG. 2A

| 13 17<br>14 18 | A=X1 | A≠X1 |
|---|---|---|
| B=X2 | ○ —<br>○ ○ | ○ —<br>✕ ○ |
| B≠X2 | ○ —<br>○ ✕ | ? —<br>? ? |

FIG. 2B

| 13 17<br>14 18 | C=Y1 | C≠Y1 |
|---|---|---|
| D=Y2 | ✕ ○<br>○ ○ | ✕ ○<br>✕ ○ |
| D≠Y2 | ✕ ○<br>○ ✕ | ? ?<br>? ? |

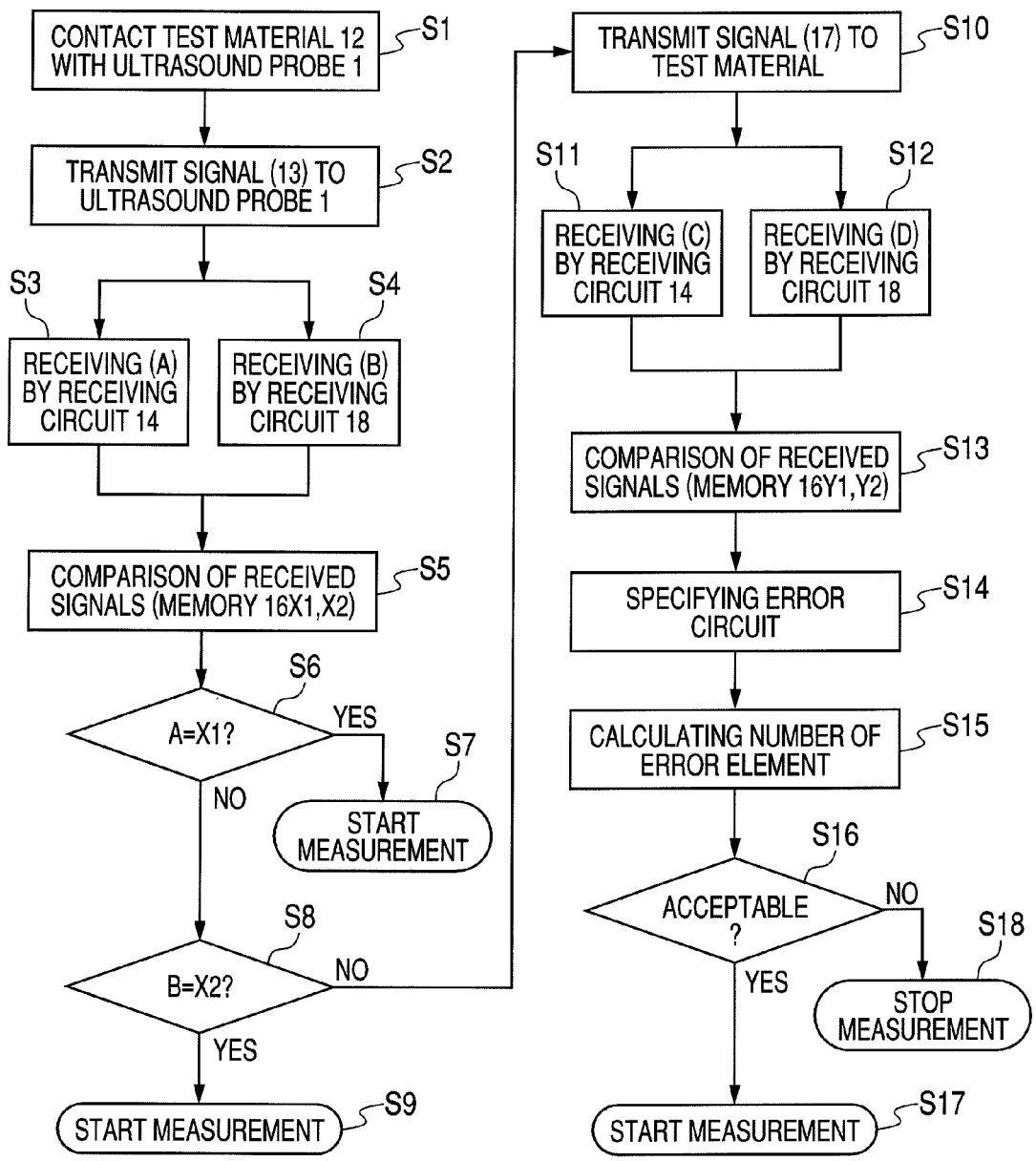

TEST METHOD OF OPERATIONS OF ULTRASONOGRAPH AND ULTRASOUND PROBE

BACKGROUND OF THE INVENTION

1. Field of the Invention

The present invention relates to a test method of operations of an ultrasonograph and an ultrasound probe, and particularly, to a test method of operations of an ultrasonograph and an ultrasound probe that can specify defective parts of the ultrasound probe.

2. Description of the Related Art

An ultrasonograph is widely used as a unit for a noninvasive acquisition of image information of the body.

The ultrasonograph delivers ultrasound transmitted from an ultrasound probe to a target material in a living body and processes a reflected wave from the target material by processing a received signal received by the ultrasound probe to create a diagnostic image.

The ultrasound probe is constituted by an array transducer formed of a plurality of oscillating elements and includes a function for transmitting and receiving ultrasound.

In recent years, the number of constituent elements of the array transducer has been increased to improve the image quality of a diagnostic image, and for example, a 2D array transducer is constituted by 128×128 oscillating elements.

Therefore, a normal operation of the ultrasound probe needs to be checked before starting diagnosis to always use the ultrasound probe in the best condition.

Conventionally, Japanese Patent Application Laid-Open No. 2002-159492 discloses the following ultrasonograph that checks the normal operation of the ultrasound probe.

More specifically, a transmission and reception surface of an ultrasound probe including a plurality of oscillating elements is brought into contact with a reflector, and the probe transmits ultrasound.

The reflector reflects the transmitted ultrasound, and the ultrasound probe receives a reflected wave.

The quality of operation of each oscillating element is determined based on the amplitude and phase of the received signal. Transmission is controlled so that the transmission is not performed to the oscillating element determined to be a defective oscillating element.

As described, the ultrasonograph of Japanese Patent Application Laid-Open No. 2002-159492 in the aforementioned example of the conventional art determines the quality of operation of each oscillating element based on the amplitude and phase of the received signal. However, the ultrasonograph cannot specify whether a defective part of the ultrasound probe is in a transmitting circuit or in a receiving circuit. As a result, an appropriate treatment may not be applied to the defective part after the quality of operation is determined.

Japanese Patent Publication No. 61-9584 discloses an abnormality determination method, in which two ultrasound probes face each other and mutually transmit and receive ultrasound, and whether a defect is in a transmission operation or in a reception operation is specified based on the received signals.

However, the example of the conventional art determines the quality based on the time difference of the received signals and the signal strength, and the quality determination of each oscillating element is inevitable. The example is inconvenient in that a determination cannot be made without two probes.

SUMMARY OF THE INVENTION

In view of the forgoing problems, an object of the present invention is to provide a test method of operations of an ultrasonograph and an ultrasound probe that can easily specify defective parts of the ultrasound probe and that can appropriately treat the defective parts.

The present invention provides a test method of an operation of an ultrasound probe that transmits and receives a signal of ultrasound for creating a diagnostic image in an ultrasonograph, the method including: bringing a test material into contact with the ultrasound probe and transmitting a first ultrasound from the ultrasound probe to the test material by a first transmitting circuit connected to the ultrasound probe; receiving, by a first receiving circuit connected to the ultrasound probe, a received signal of a reflected wave of the first ultrasound received by the test material and receiving, by a second receiving circuit connected to the test material, a received signal of the first ultrasound received by the test material; and comparing the received signals with each normal received signal stored in a memory and determining whether the operation of the ultrasound probe is normal or defective based on the comparison result.

The test method of the operation of the ultrasound probe described above can further include if it cannot be determined whether the first transmitting circuit and the first receiving circuit are normal or defective in the determining step: bringing a test material into contact with the ultrasound probe and transmitting a second ultrasound from the test material to the ultrasound probe by a second transmitting circuit connected to the test material; receiving by the first receiving circuit a received signal of the second ultrasound received by the ultrasound probe and receiving by the second receiving circuit a received signal of a reflected wave of the second ultrasound received by the ultrasound probe; and comparing the received signals with each normal received signal stored in a memory and determining whether the first transmitting circuit and the first receiving circuit are normal or defective based on the comparison result.

The present invention can realize a test method of operations of an ultrasonograph and an ultrasound probe that can easily specify defective parts of the ultrasound probe and that can appropriately treat the defective parts.

Further features of the present invention will become apparent from the following description of exemplary embodiments with reference to the attached drawings.

BRIEF DESCRIPTION OF THE DRAWINGS

FIGS. 2A and 2B depict a quality determination result in a first testing step (FIG. 2A) and a quality determination result in a second testing step (FIG. 2B) in matrix.

FIG. 3 is a flow chart for describing a test method of an operation of an ultrasound probe according to an embodiment of the present invention.

DESCRIPTION OF THE EMBODIMENTS

Figure 1:
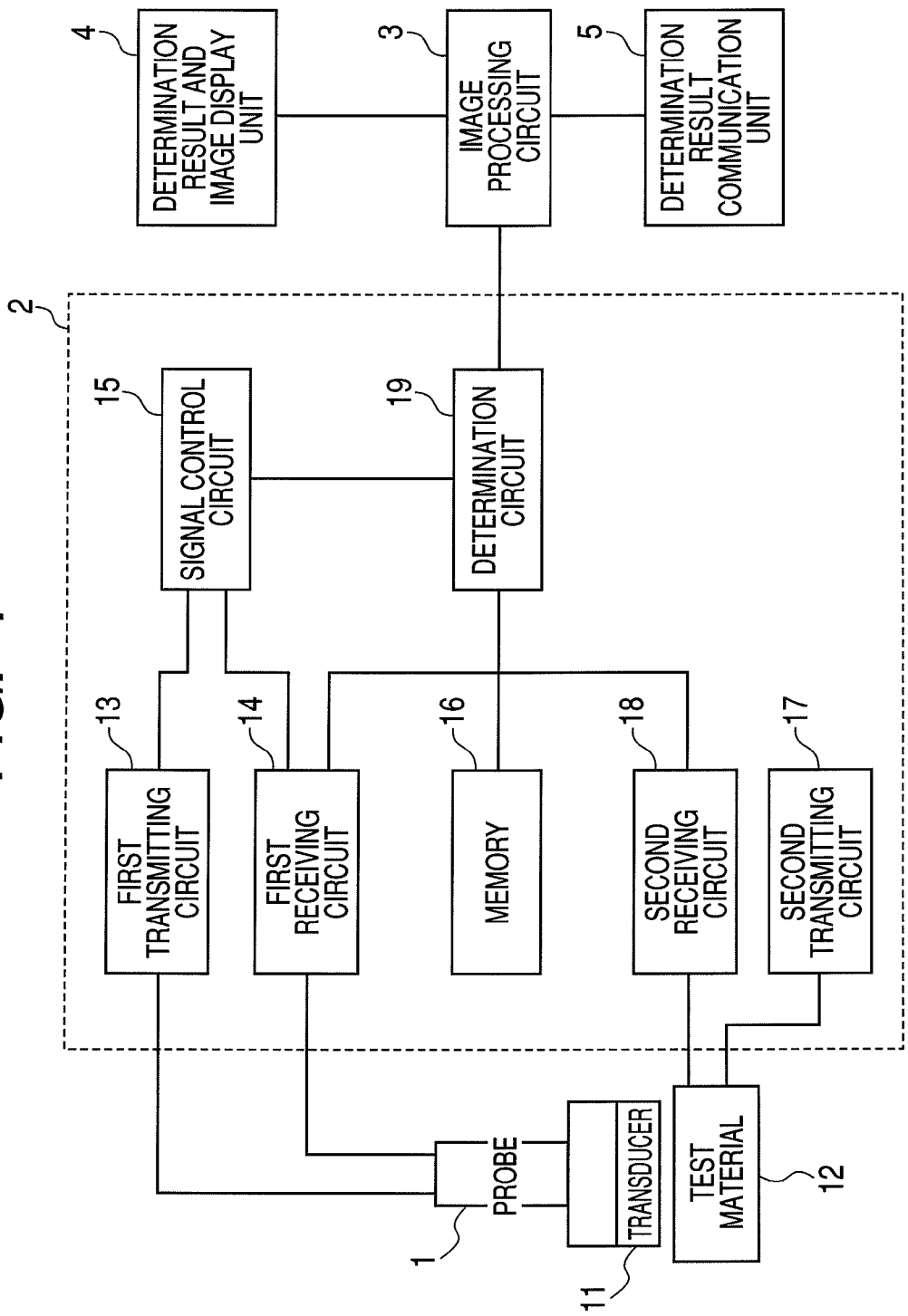
FIG. 1 is a block diagram for describing an overall configuration of an ultrasonograph according to an embodiment of the present invention.

Preferred embodiments of the present invention will now be described in detail in accordance with the accompanying drawings.

(Configuration of Ultrasonograph)

A configuration example of an ultrasonograph according to an embodiment of the present invention will now be described.

FIG. 1 is a block diagram for describing an overall configuration of the ultrasonograph of the present embodiment.

In FIG. 1, reference numeral 1 denotes an ultrasound probe, reference numeral 2 denotes a transmission and reception signal control unit, reference numeral 3 denotes an image processing circuit, reference numeral 4 denotes a determination result and image display unit, and reference numeral 5 denotes a communication unit that transmits a determination result to the outside.

Reference numeral 11 denotes an array transducer, reference numeral 12 denotes a test material, reference numeral 13 denotes a first transmitting circuit, and reference numeral 14 denotes a first receiving circuit.

Reference numeral 15 denotes a signal control circuit, reference numeral 16 denotes a normal signal storage memory, reference numeral 17 denotes a second transmitting circuit, reference numeral 18 denotes a second receiving circuit, and reference numeral 19 denotes a determination circuit.

As shown in FIG. 1, the ultrasonograph of the present embodiment includes the ultrasound probe 1 in contact with the surface of a living body for use and the transmission and reception signal control unit 2 connected to the ultrasound probe 1. The ultrasound probe 1 is constituted by the array transducer 11 formed of a plurality of oscillating elements.

The ultrasonograph further includes the image processing circuit 3 connected to a determination output unit of the transmission and reception signal control unit 2, the image display unit 4 connected to the image processing circuit 3, and the communication unit 5 that transmits the determination result to the outside.

In the present invention, the "oscillating elements" denote one unit that constitutes the array transducer 11 of the ultrasound probe and that is connected to a transmitting circuit and a receiving circuit to transmit and receive ultrasound. Elements serve as the oscillating elements if the array transducer is a capacitive electromechanical transducer (CMUT).

The test material 12 is brought into contact with the wavefront of the ultrasound probe 1 to perform an operational test of the oscillating elements of the ultrasound probe.

The "test material" in the present invention is a material that emits a reflected wave to ultrasound radiation.

Examples of the test material 12 include a reflection sheet such as a metal sheet and an ultrasound phantom in which a target material is created by metal or plastic such as urethane. The "ultrasound phantom" is a human phantom created by a material with properties equivalent to skin or tissue against ultrasound.

The transmission and reception control unit 2 includes the first transmitting circuit 13 and the first receiving circuit 14 connected to the ultrasound probe 1, the signal processing circuit 15, and the memory 16 storing normal signals.

The transmission and reception signal control unit 2 further includes the second transmitting circuit 17 and the second receiving circuit 18 connected to the test material 12 and the determination circuit 19 that determines the quality of the operation of the ultrasound probe 1.

(Transmitting and Receiving Circuits)

The first transmitting circuit 13 is connected to the ultrasound probe 1 and is capable of transmitting ultrasound from the ultrasound probe 1 by transmitting a signal to the ultrasound probe. Upon transmission of a signal to the ultrasound probe 1 in an operational test, the test material is brought into contact with the ultrasound probe, and ultrasound is transmitted to the test material from the ultrasound probe.

The second transmitting circuit 17 is connected to the test material 12 and is capable of transmitting ultrasound from the test material 12 by transmitting a signal to the test material. The test material is brought into contact with the ultrasound probe in an operational test, and a signal is transmitted from the second transmitting circuit to the test material to transmit ultrasound from the test material to the ultrasound probe.

The first receiving circuit 14 is connected to the ultrasound probe. The first receiving circuit 14 receives a received signal of a reflected wave of ultrasound received by the test material by a signal transmitted from the first transmitting circuit and receives a received signal of ultrasound received by the ultrasound probe by a signal transmitted from the second transmitting circuit.

The second receiving circuit 18 is connected to the test material. The second receiving circuit 18 receives a received signal of ultrasound received by the test material by a signal transmitted from the first transmitting circuit and receives a received signal of a reflected wave of ultrasound received by the ultrasound probe by a signal transmitted from the second transmitting circuit.

(Test Method of Operation of Ultrasound Probe)

A test method of an operation of the ultrasound probe in the present embodiment will now be described.

The test method of an operation of the ultrasound probe in the present embodiment includes: a first testing step (S1 to S9 of FIG. 3) performed by the first transmitting circuit 13 by transmitting ultrasound from the ultrasound probe to the test material; and a second testing step (S10 to S14 of FIG. 3) performed by the second transmitting circuit 17 by transmitting ultrasound from the test material to the ultrasound probe.

FIG. 3 is a flow chart for describing the test method of an operation of the ultrasound probe in an embodiment of the present invention.

FIG. 2A illustrates a quality determination result in the first testing step in matrix, and FIG. 2B illustrates a quality determination result in the second testing step in matrix. In the fields, the upper left portion corresponds to the first transmitting circuit 13, the lower left portion corresponds to the first receiving circuit 14, the upper right portion corresponds to the second transmitting circuit 17, and the lower right portion corresponds to the second receiving circuit 18. In the fields, "O" denotes normal, and "x" denotes defective.

(First Testing Step)

The first testing step will be described first.

The test material 12 is brought into contact with the ultrasound probe 1 (S1), and the first transmitting circuit 13 connected to the ultrasound probe transmits a first ultrasound from the ultrasound probe to the test material (S2).

The first receiving circuit 14 connected to the ultrasound probe receives a received signal of a reflected wave of the first ultrasound received by the test material (S3). At the same time, the second receiving circuit 18 connected to the test material receives a received signal of the first ultrasound received by the test material (S4).

The received signals and normal received signals of the received signals stored in the memory are compared, and based on the comparison result, whether the operation of the ultrasound probe is normal or defective is determined (S5).

The determination method will now be described specifically.

A first received signal received by the first receiving circuit will be referred to as A, and a normal received signal corresponding to the first received signal will be referred to as X1. A second received signal received by the second receiving circuit will be referred to as B, and a normal received signal corresponding to the second received signal will be referred to as X2. The signals X1 and X2 are stored in the memory 16.

The method will be described with reference to FIG. 2A. If A corresponds to X1, and B corresponds to X2, it can be recognized that the first transmitting circuit has normally transmitted ultrasound and that the first and second receiving circuits have normally received the ultrasound. As a result, both the first transmitting circuit 13 and the first receiving circuit 14 can be specified to be normal.

If A corresponds to X1, and B does not correspond to X2, it can be recognized that the first transmitting circuit has normally transmitted ultrasound and the first receiving circuit has normally received the ultrasound, but the second receiving circuit has not normally received the ultrasound. As a result, it can be specified that the second receiving circuit is defective, but the first transmitting circuit 13 and the first receiving circuit 14 are both normal.

If A does not correspond to X1, and B corresponds to X2, it can be recognized that the first transmitting circuit has normally transmitted ultrasound, the first receiving circuit has not normally received the ultrasound, and the second receiving circuit has normally received the ultrasound. As a result, it can be specified that the first transmitting circuit 13 is normal, but the first receiving circuit 14 is defective.

Lastly, if A does not correspond to X1 as well as B does not correspond to X2, whether the first transmitting circuit has normally transmitted the ultrasound cannot be specified. Therefore, which circuit is normal cannot be specified. For example, the first and second receiving circuits are both defective if the first transmitting circuit 13 is normal, and whether the first and second receiving circuits are defective is unclear if the first transmitting circuit 13 is defective.

Based on the forgoing, whether A=X1 is determined in S6, and the first transmitting circuit 13 and the first receiving circuit 14 of the ultrasound probe are both normal based on FIG. 2A if the answer is Y. Therefore, the measurement can be started as usual (S7).

On the other hand, if the answer is N, whether B=X2 is determined (S8). If the answer is Y, the first transmitting circuit 13 is normal although the first receiving circuit 14 is defective. Therefore, the measurement can be started if the defect of the receiving circuit is within an acceptable level (S9). Whether the defective level is within the acceptable level can be determined by, for example, performing a test for each element described later. If the answer is N, the process moves to the second testing step described below.

(Second Testing Step)

In that case, the second testing step described below will be performed. The second testing step will now be described, in which the second transmitting circuit 17 transmits ultrasound from the test material to the ultrasound probe.

The second testing step is performed if it cannot be determined whether the first transmitting circuit 13 and the first receiving circuit 14 are normal or defective in the first testing step.

The test material 12 is first brought into contact with the ultrasound probe 1, and the second transmitting circuit 17 connected to the test material transmits a second ultrasound from the test material to the ultrasound probe (S10).

The first receiving circuit 14 receives a received signal of the second ultrasound received by the ultrasound probe (S11). At the same time, the second receiving circuit 18 receives a received signal of a reflected wave of the second ultrasound received by the ultrasound probe (S12).

The received signals are compared with normal received signals of the received signals stored in the memory (S13), and based on the comparison result, whether the first transmitting circuit and the first receiving circuit are normal or defective is determined (S14).

The determination method will now be described specifically.

A third received signal received by the first receiving circuit will be referred to as C, and a normal received signal corresponding to the third received signal will be referred to as Y1. A fourth received signal received by the second receiving circuit will be referred to as D, and a normal received signal corresponding to the second received signal will be referred to as Y2. The signals Y1 and Y2 are stored in the memory 16.

The method will be described with reference to FIG. 2B. If C corresponds to Y1, and D corresponds to Y2, it can be recognized that the second transmitting circuit has normally transmitted ultrasound, and the first and second receiving circuits have normally received the ultrasound. In this case, it can be determined that there is an abnormality in the first transmitting circuit, because it can be determined that the first and second receiving circuits are normal. As a result, it can be specified that the first transmitting circuit 13 is defective and the first receiving circuit 14 is normal.

If C corresponds to Y1, and D does not correspond to Y2, it can be recognized that the first transmitting circuit has normally transmitted ultrasound, the first receiving circuit has normally received the ultrasound, but the second receiving circuit has not normally received the ultrasound. In this case, it can be determined that there is an abnormality in the first transmitting circuit, because it can be determined that the first receiving circuit is normal. As a result, it can be specified that the first transmitting circuit 13 is defective and the first receiving circuit 14 is normal.

If C does not correspond to Y1, and D corresponds to Y2, it can be recognized that the first transmitting circuit has normally transmitted ultrasound, the first receiving circuit has not normally received the ultrasound, and the second receiving circuit has normally received the ultrasound. In this case, it can be determined that there is an abnormality in the first transmitting circuit, because it can be determined that the second receiving circuit is normal. As a result, the first transmitting circuit 13 and the first receiving circuit 14 can be specified to be defective.

Lastly, if C does not correspond to Y1 as well as C does not correspond to Y2, which circuit is normal cannot be specified because whether the second transmitting circuit has normally transmitted the ultrasound cannot be specified. This is only the case in which whether the first transmitting circuit 13 and the first receiving circuit 14 are normal or defective cannot be determined.

However, the specification is possible in all cases if the second transmitting circuit and the second receiving circuit are assumed to be normal. More specifically, if A≠X1 and B≠X2 in the first testing step, it can be logically determined that the first transmitting circuit 13 is defective if the second receiving circuit is normal. The quality of the first receiving circuit 14 can be specified in the second testing step. In other words, since D=Y2 in every case of the second testing step, there is no case in which the specification is impossible.

Therefore, whether the first transmitting circuit and the first receiving circuit are normal can be always specified by the first and second testing steps if the test is performed by the second transmitting circuit and the second receiving circuit that are already known to be normal.

(Execution Unit of Operational Test)

In the first and second testing steps, the transmission of ultrasound from the ultrasound probe and the reception of ultrasound by the ultrasound probe can be performed across all the plurality of oscillating elements of the ultrasound probe. In that case, the received signals A and C received by the first receiving circuit are signals in which signals obtained by the plurality of receiving elements are combined. For example, specifically, the received signals are phased and added from receiving circuits corresponding to the oscillating elements to obtain a received signal. The memory 16 stores a normal received signal corresponding to the received signal.

In the present embodiment, the quality of the entire probe can be determined first, instead of the quality of each element. This is realized by implementing a determination method in which the normal received signals are stored in the memory in advance and verified.

In the present specification, the "normal received signal" denotes a received signal obtained when the related transmitting/receiving circuits are normal in a specific known condition.

The first and second testing steps can be individually performed to each of the plurality of oscillating elements of the ultrasound probe if one of the first transmitting circuit and the first receiving circuit of the ultrasound probe is determined to be defective in the first and second testing steps. In this way, the quality of each element can be determined only when there is a defect, and an economical and accurate measurement is realized.

If an error circuit is specified in the second testing step (S14), one of the first transmitting circuit 13 and the first receiving circuit 14 is defective. Thus, testing can be performed for each oscillating element as described (S15).

In the individual first and second testing steps for each oscillating element, only one oscillating element transmits ultrasound, and an oscillating element of a receiving circuit corresponding to the oscillating element is evaluated element by element.

In the present invention, the concept of the "first transmitting/receiving circuits and second transmitting/receiving circuits" differs in the test across all the plurality of oscillating elements and in the test of each oscillating element. More specifically, a phased and added received signal is evaluated when the test is performed entirely, while a received signal of each oscillating element is evaluated when the test is performed for each oscillating element. The entire mechanism including a phase addition circuit can be perceived as the first receiving circuit when the test is performed across all oscillating elements. A receiving circuit corresponding to the oscillating element can be perceived as the first receiving circuit when the individual testing is performed. In either case, the method for determining the quality of circuit is the same as described above.

When the quality is determined for each oscillating element, whether the number of defective elements is within an acceptable level for the measurement is determined (S16). The measurement can be started if the quality of the transmitting circuit and/or the receiving circuit of each oscillating element is within a predetermined acceptable level (S17), and the measurement can be canceled if the quality is not within the acceptable level (S18). In one embodiment, the measurement is canceled if 20% of the oscillating elements are defective.

In this way, the determination circuit 19 as a determination unit executes the step of determining the influence on the image generation due to defective operations of the ultrasound probe. The signal control circuit 15 is the signal control unit that controls the transmission and reception signals of the ultrasound probe upon measurement based on the determination result.

There is a possibility of some kind of defect if an error circuit cannot be specified in the second testing step. Therefore, although not shown in FIG. 3, the test can be performed again using second transmitting/receiving circuits that are already known to be normal. However, there is no such a case if the second transmitting/receiving circuits that are known to be normal are used from the beginning.

The image processing circuit 3 displays the determination result and the image on a display unit. Quick maintenance is possible as the communication unit 5 reports canceling of measurement to the outside if the measurement is canceled.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2008-107866, filed Apr. 17, 2008, and 2009-094997, filed Apr. 9, 2009, which are hereby incorporated by reference herein in their entirety.

What is claimed is:

1. A test method of an operation of an ultrasound probe that transmits and receives a signal of ultrasound for creating a diagnostic image in an ultrasonograph, the method comprising:
   bringing a test material into contact with the ultrasound probe and transmitting a first ultrasound from the ultrasound probe to the test material by a first transmitting circuit connected to the ultrasound probe;
   receiving, by a first receiving circuit connected to the ultrasound probe, a received signal of a reflected wave of the first ultrasound received by the test material and receiving, by a second receiving circuit connected to the test material, a received signal of the first ultrasound received by the test material; and
   comparing the received signals with each normal received signal stored in a memory and determining whether the operation of the ultrasound probe is normal or defective based on a result of the comparison.

2. The test method of the operation of the ultrasound probe according to claim 1, further comprising:
   if performance of said determining step does not result in a determination as to whether the first transmitting circuit and the first receiving circuit are normal or defective:
   bringing the test material into contact with the ultrasound probe and transmitting a second ultrasound from the test material to the ultrasound probe by a second transmitting circuit connected to the test material;
   receiving by the first receiving circuit a received signal of the second ultrasound received by the ultrasound probe and receiving by the second receiving circuit a received signal of a reflected wave of the second ultrasound received by the ultrasound probe; and
   comparing the received signals with each normal received signal stored in a memory and determining whether the first transmitting circuit and the first receiving circuit are normal or defective based on a result of the comparison.

3. The test method according to claim 2, wherein the transmission of ultrasound from the ultrasound probe and the reception of ultrasound by the ultrasound probe are performed across all of a plurality of oscillating elements of the ultrasound probe, and
   the received signal received by the first receiving circuit is a signal formed by combining each signal obtained by a plurality of receiving elements.

4. The test method according to claim 3, wherein, if one of the first transmitting circuit and the first receiving circuit of the ultrasound probe is determined to be defective,
   for each of the plurality of oscillating elements of the ultrasound probe:

the test material is brought into contact with the ultrasound probe and a second ultrasound is transmitted from the test material to the ultrasound probe by the second transmitting circuit connected to the test material;

the first receiving circuit receives a received signal of the second ultrasound received by the ultrasound probe and the second receiving circuit receives a received signal of a reflected wave of the second ultrasound received by the ultrasound probe; and the received signals are compared with each normal received signal stored in a memory and a determination is made as to whether the first transmitting circuit and the first receiving circuit are normal or defective based on a result of the comparison.

5. The test method according to claim 4, wherein creation of the diagnostic image is started if the quality of a transmitting circuit and/or a receiving circuit of each of the plurality of oscillating elements is within a predetermined acceptable level, and creation of the diagnostic image is canceled if the quality is not within the acceptable level.

6. An ultrasonograph that comprises an ultrasound probe for transmitting and receiving a signal of ultrasound and that processes a received signal by the ultrasound probe to create a diagnostic image, the ultrasonograph comprising:

a first transmitting circuit that is connected to the ultrasound probe and that transmits a signal to the ultrasound probe, with a test material in contact with the ultrasound probe;

a second transmitting circuit that is connected to the test material and that transmits a signal to the test material in contact with the ultrasound probe;

a first receiving circuit that receives a received signal of a reflected wave of ultrasound received by the test material by the signal transmitted from said first transmitting circuit and that receives a received signal of ultrasound received by the ultrasound probe by the signal transmitted from said second transmitting circuit, said first receiving circuit being connected to the ultrasound probe;

a second receiving circuit that receives a received signal of ultrasound received by the test material by the signal transmitted from said first transmitting circuit and that receives a received signal of a reflected wave of ultrasound received by the ultrasound probe by the signal transmitted from said second transmitting circuit, said second receiving circuit being connected to the test material; and a determination unit that compares the received signals received by said first and second receiving circuits with each normal received signal stored in a memory to determine a defect of the operation of the ultrasound probe.

7. The ultrasonograph according to claim 6, further comprising a signal control unit that controls transmission and reception signals of the ultrasound probe based on a determination result from said determination unit.

8. The ultrasonograph according to claim 6, wherein said determination unit includes a determination part that determines an influence on the image generation due to a defect in the operation of the ultrasound probe.

9. The ultrasonograph according to claim 6, further comprising a display unit that displays a determination result from said determination unit.

10. The ultrasonograph according to claim 6, further comprising a communication unit that transmits a determination result from said determination unit to the outside.

11. The ultrasonograph according to claim 6, wherein the test material is a metal sheet or a phantom.

* * * * *